US00PP13746P29

(12) United States Plant Patent
Zwetzig et al.

(10) Patent No.: US PP13,746 P2
(45) Date of Patent: Apr. 29, 2003

(54) HIBISCUS PLANT NAMED 'DREAMCATCHER'

(76) Inventors: Gretchen Angela Zwetzig, 8101 S. 14th St., Lincoln, NE (US) 68512; David Whitman Fleming, deceased, late of Lincoln, NE (US), by Gretchen Zwetzig, legal representative ( * ) Notice: Subject to any disclaimer, the term of this patent is extended or adjusted under 35 U.S.C. 154(b) by 0 days.

(21) Appl. No.: 10/207,252

(22) Filed: Jul. 30, 2002

(51) Int. Cl.[7] ..... A01H 5/00

(52) U.S. Cl. ..... Plt./257
(58) Field of Search ..... Plt./257

*Primary Examiner*—Bruce R. Campell
*Assistant Examiner*—W C Haas

(57) ABSTRACT

A new and distinct cultivar of winter hardy hibiscus plant named 'Dreamcatcher' is the result of a unique hybridization. This new and distinct cultivar is characterized primarily as to novelty by, its extreme cold hardiness to Zone 4, large, thick-textured, "Quilted" pink flowers and its "Maple-shaped" green leaves with a purple cast, compactness of about 3 feet, its vigorous and uniform growth habit, and its floriferous nature from midsummer until frost.

1 Drawing Sheet

BOTANICAL CLASSIFICATION

*Hibiscus moscheutos×H. coccineus.*

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined, "Maple-shaped" green leaves with a purple cast and relatively smooth margins which combined compliments the landscape;
(b) Large flowers that are outstanding for their pink overlapping petals with a "Quilted" appearance (flowers are segmented into squares which are puffed up;
(c) The plant being very floriferous with flowers that stay open at least one full day;
(d) The plant being medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Dreamcatcher' was the result of a 40-year breeding program. Its ancestry includes *Hibiscus moscheutos* and *Hibiscus coccineus*. More specifically, the plant resulted from multiple crossings with 'Pink Perfection' a Fleming *Hibiscus moscheutos* (nonpatented) and '42' a Fleming *Hibiscus coccineus* (nonpatented). The seedling which most nearly met all of the above named standards was selected.

This new plant first bloomed in the summer of 1990 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This Hardy Hibiscus plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown in the attached photograph. More specifically, the photograph is a close-up of the flower and the leaf.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The R.H.S Colour Chart, while general color recitations are consistent with ordinary American color terminology.

'Dreamcatcher' has not been observed under all possible environment conditions. It is to be understood that the phenotype may vary significantly with variations in environment such as temperature, light intensity, and day length, without, however any difference in genotype of the plant. The following botanical characteristics and observations are gathered from the plant when grown in Lincoln, Nebr. (USDA Zone 4).

THE PLANT

Parentage:
*Seed parent.—Hibiscus moscheutos*, 'Pink Perfection' an unpatented Fleming seedling.
*Pollen parent.—Hibiscus coccineus* '42' an unpatented Fleming seedling.
Origin: A selected seedling from stated cross.
Type of plant: Hardy, herbaceous perennial.
Classification: Variety of Hardy Hibiscus plant.

Propagation: Relatively easy to propagate; holds its distinguishing characteristics through successive cuttings and division.

Size: About 3–3½ feet tall and about 3 ft. wide.

Form: Symmetrical annual growth from perennial roots.

Habit: Upright and uniformly branched.

Growth: Vigorous; medium and compact. Full grown (3–3½ ft.) in 2 years.

Hardiness: Hardy to at least −30 degrees Fahrenheit.

General health: Plant is very disease resistant against rot, aphids, spider mites, scale, white fly, etc.; sturdy through excessive drought, rain, or wind.

Propagation: Relatively easy and fast rooting in approximately 2 weeks.

Foliage:

1. *Arrangement.*—Alternate.
2. *Shape.*—Juvenile: Variable: 3-lobed, "Maple-like" leaves with a rounded base shape. Mature: Refined, "Maple-like", 3–5 lobed leaf with entire to mildly serrate margins and acute apices; rounded base.
3. *Size.*—Mature leaf (petiole base to apex): Length is about 4¼ inches or 10.5 cm, width is about 3¾ inches or 9.7 cm.
4. *Color.*—Young leaves (upper side): 137-A, (purple cast) between N-92 and N-187. Mature leaves: (upper side): 137-A, (purple cast) between N-92 and N-187. Veins: 191-A. Coloration of the lower leaf surface: Closest to 191-A.
5. *Surface texture.*—Low to medium sheen.
6. *Petiole length.*—About 1¼ inches or 3.5 cm.
7. *Petiole color.*—191-A.

Stems: The stems are stout at the base, becoming more slender toward the apices; coloration is consistent with the petiole.

THE FLOWER

Blooming period: Profuse from July until frost.

Flower diameter: Medium to large; about 11 inches (25 cm).

Borne: Singly in leaf axils, from midpoint of stems upward.

Bloom duration: Individual bloom lasts at least one full day.

Form: Campanulate; petals are also very overlapping.

Bud:

1. *Length.*—About 2 inches (or 5 cm) on day before opening.
2. *Color.*—63-A.
3. *Surface texture.*—Semi-glabrous.
4. *Duration.*—One to two weeks.

Corolla: Having 5 petals.

1. *Petal character and dimensions.*—Campanulate and very overlapping. Length is about 5½ inches or 12.7 cm. Width is about 5 inches or 12 cm.
2. *Coloration.*—Pale pink petals. (a) Pale pink petals: Between 65-A and 69-C. Coloration of lower petal surface: Slightly lighter than 69-C. (b) Veination in petals: 46-A. (c) Eye Zone: 46-A.
3. *Texture.*—Smooth.
4. *Substance.*—Thick.
5. *Shape.*—Campanulate and very overlapping.

Reproductive organs:

1. *Staminal column.*—Stamen along basal two-thirds. Stamen length: About 1¾ inches (or 4.8 cm). Stamen color: 67-A, and 69-B. Pollen color: 8-B.
2. *Style.*—Terminates upper one-third of staminal coumn. Stigmnatic lobe color: 155-B.

Calyx: Connate at the base; about 3½ inches (or 8.5 cm) in length. Color: Medium green.

Stipules: None.

Epicalyx: Whorl of bracts.

1. *Shape.*—10 to 12 slender, sword-shaped bractlets.
2. *Length.*—About 1 inch (or 1.5 cm).
3. *Color.*—43-A.

Penduncle:

1. *Length.*—About 2¾ inches (or 6 cm).
2. *Strength.*—Stiff and sturdy.
3. *Color.*—Light to medium green with slight reddish-purple cast.

GENERAL OBSERVATIONS

This plant, as a hybridized Hardy Hibiscus, is valuable to the landscape market for its improvements in uniquely textured and colored pink flowers, refined, "Maple-like", green with a purple cast foliage on a much more compact plant, its all-around vigor, good breaking action, and adaptation to extreme environments, including the ability to consistently survive winter temperatures of at least −30 degrees Fahrenheit.

It is claimed:

1. A new and distinct cultivar of Hardy Hibiscus plant, as herein shown and described.

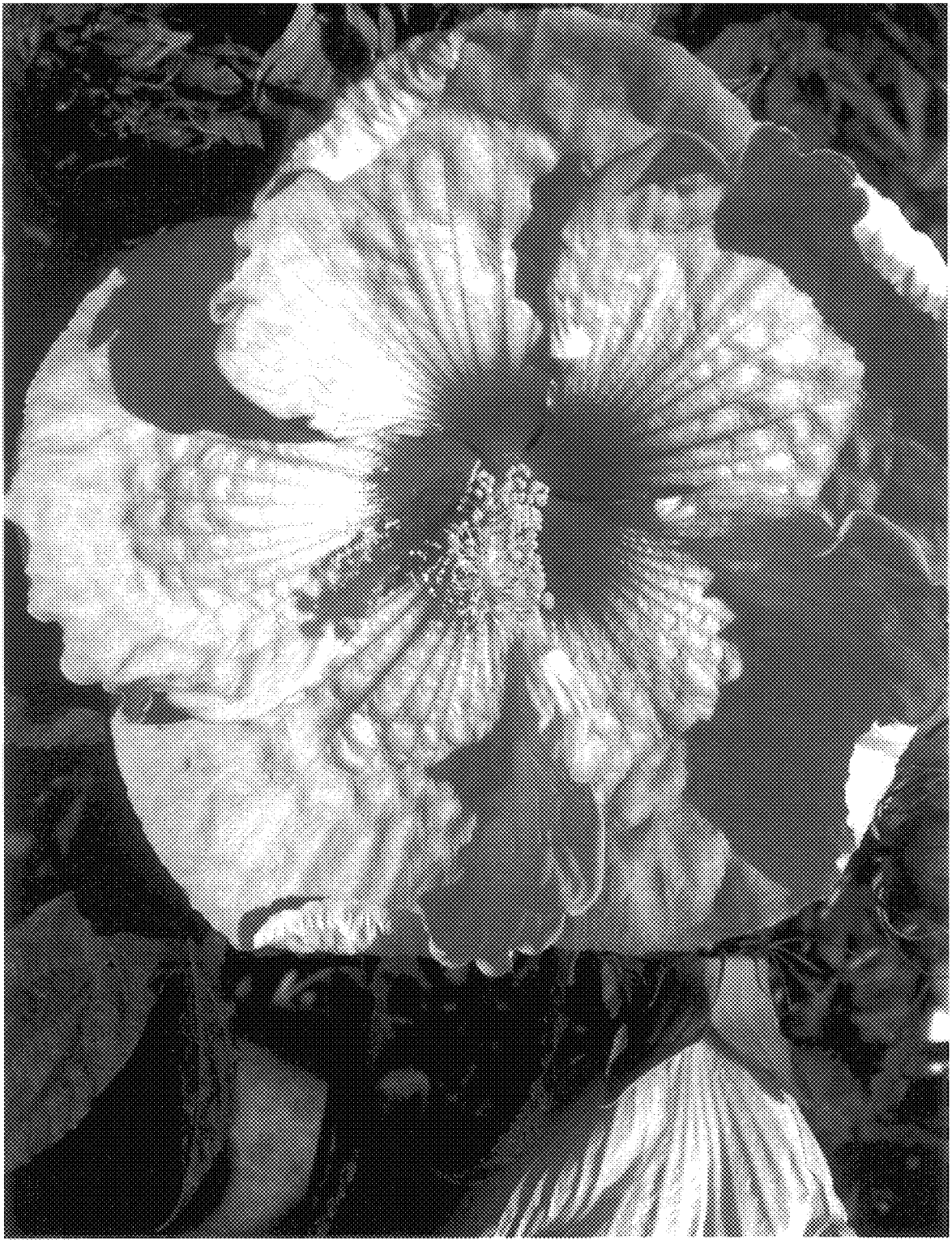

* * * * *